(12) United States Patent
Cho et al.

(10) Patent No.: US 9,084,785 B2
(45) Date of Patent: Jul. 21, 2015

(54) COMPOSITION FOR ACCELERATING CHANGE IN MUSCLE TYPE

(71) Applicant: AMOREPACIFIC CORPORATION, Seoul (KR)

(72) Inventors: Si Young Cho, Seoul (KR); Ji Hae Lee, Gyeonggi-do (KR); Il Hong Bae, Gyeonggi-do (KR); Min Jeong Song, Gyeonggi-do (KR); Hyeon Ju Yeo, Seoul (KR); Dae Bang Seo, Gyeonggi-do (KR); Wan Gi Kim, Gyeonggi-do (KR); Sang Jun Lee, Gyeonggi-do (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 14/147,102

(22) Filed: Jan. 3, 2014

(65) Prior Publication Data

US 2014/0120187 A1    May 1, 2014

Related U.S. Application Data

(62) Division of application No. 13/638,813, filed as application No. PCT/KR2011/002413 on Apr. 6, 2011, now Pat. No. 8,652,538.

(30) Foreign Application Priority Data

Apr. 6, 2010    (KR) .................. 10-2010-0031473

(51) Int. Cl.

| | | |
|---|---|---|
| *A01N 65/00* | (2009.01) | |
| *A61K 36/481* | (2006.01) | |
| *A61K 36/00* | (2006.01) | |
| *A61K 36/185* | (2006.01) | |
| *A61K 36/282* | (2006.01) | |
| *A61K 36/355* | (2006.01) | |
| *A61K 36/44* | (2006.01) | |
| *A61K 36/488* | (2006.01) | |
| *A61K 36/537* | (2006.01) | |
| *A61K 36/54* | (2006.01) | |
| *A61K 36/67* | (2006.01) | |
| *A61K 36/70* | (2006.01) | |
| *A61K 36/73* | (2006.01) | |
| *A61K 36/752* | (2006.01) | |
| *A61K 36/815* | (2006.01) | |
| *A61K 36/882* | (2006.01) | |
| *A61K 36/9064* | (2006.01) | |
| *A61K 31/202* | (2006.01) | |
| *A61K 36/424* | (2006.01) | |
| *A61K 45/06* | (2006.01) | |

(52) U.S. Cl.
CPC ............ *A61K 36/481* (2013.01); *A61K 31/202* (2013.01); *A61K 36/00* (2013.01); *A61K 36/185* (2013.01); *A61K 36/282* (2013.01); *A61K 36/355* (2013.01); *A61K 36/424* (2013.01); *A61K 36/44* (2013.01); *A61K 36/488* (2013.01); *A61K 36/537* (2013.01); *A61K 36/54* (2013.01); *A61K 36/67* (2013.01); *A61K 36/70* (2013.01); *A61K 36/73* (2013.01); *A61K 36/752* (2013.01); *A61K 36/815* (2013.01); *A61K 36/882* (2013.01); *A61K 36/9064* (2013.01); *A61K 45/06* (2013.01)

(58) Field of Classification Search
CPC ...................................................... A61K 36/00
USPC ........................................................ 424/725
See application file for complete search history.

(56) References Cited

U.S. PATENT DOCUMENTS

| | | |
|---|---|---|
| 2010/0260733 A1 | 10/2010 | Qi |
| 2011/0138488 A1 | 6/2011 | Zhang et al. |
| 2011/0144009 A1 | 6/2011 | Boss et al. |

FOREIGN PATENT DOCUMENTS

| | | |
|---|---|---|
| JP | 2009-256309 A | 11/2009 |
| KR | 10-2007-0004999 A | 1/2007 |
| KR | 10-2008-0003931 A | 1/2008 |
| KR | 10-0818586 B1 | 4/2008 |
| KR | 10-2009-0113554 A | 11/2009 |
| KR | 10-2011-0080470 A | 7/2011 |

OTHER PUBLICATIONS

Ewa Ehrenboger et al., Regulation to Skeletal Muscle Physiology and Metabolism by Peroxisome Proliferator-Activated Receptor δ, *Pharmacological Reviews*, 2009, vol. 61(33), pp. 373-393.

U.J. Jung et al., "The Anti-diabetic Effects of Ethanol Extract from Two Variants of *Artemisia princeps* Pampanini in C57BL/KsJ-db/db Mice," *Food and Chemical Toxicology*, 2007, vol. 45(10), pp. 2022-2029.

*Primary Examiner* — Michael Meller
(74) *Attorney, Agent, or Firm* — Dickstein Shapiro LLP

(57) ABSTRACT

The present invention provides a composition for accelerating a change in muscle type, increasing the amount of muscle, strengthening muscle, enhancing athletic abilities, reducing lipids, suppressing the accumulation of lipids, lowering blood sugar, controlling body weight or lowering body weight, containing a PPAR-δ promoter, an AMPK promoter and a PGC1-α promoter as an active ingredient.

2 Claims, 12 Drawing Sheets

COMPOSITION FOR ACCELERATING CHANGE IN MUSCLE TYPE

CROSS REFERENCE TO RELATED APPLICATION

This application is a divisional application of U.S. application Ser. No. 13/638,813, filed Oct. 1, 2012, and is incorporated in its entirety by reference herewith.

TECHNICAL FIELD

The present disclosure relates to a composition for accelerating a change in muscle type.

BACKGROUND ART

Muscles generated through aerobic exercise consume body fats by using fats rather than carbohydrates as primary energy source. Since less carbohydrate is consumed, the blood sugar level is maintained and less hunger is experienced. In addition, since ATP is produced from fats rather than from carbohydrates, less reactive oxygen species are produced during the ATP generation and cell damage by the reactive oxygen species can be prevented. However, not all exercise exhibits such effect. Only aerobic exercises such as running and bicycling can provide such effect since they change the fast-twitch type muscles into slow-twitch type.

Human muscle consists of fast-twitch (type II) muscles and slow-twitch (type I) muscles approximately half-and-half. The fast-twitch muscle looks white since it lacks myoglobin and uses carbohydrates as primary energy source. This type of muscle is mainly formed through anaerobic exercise such as weight training. It has large muscle mass and is used for quick motion. In contrast, the slow-twitch muscle looks red because of myoglobin and uses fats instead of carbohydrates as primary energy source. It is mainly formed through aerobic exercise, has small muscle mass and is used for slow, long motion. The slow-twitch muscles enable exercise for a long time since they are rich in mitochondria and have high mitochondrial activity and thus resistance to fatigue is improved.

In general, sprinting athletes have fast-twitch muscles and slow-twitch muscles at a proportion of about 70:30 and have well-developed upper bodies. In contrast, marathoners usually have fast-twitch muscles and slow-twitch muscles at a proportion of about 30:70 and tend to have slim bodies. Marathoners are undersized than non-athletes of the same body weight (fast-twitch muscle:slow-twitch muscle=about 50:50) because muscles are about 5 times smaller in volume than fats of the same weight. To have a body of a marathoner through aerobic exercise, one should take exercise of 65-75% intensity based on the maximum heart rate for over 6 weeks, at least 3 times a week, more than 40 minutes a day, which is not so easy.

DISCLOSURE

Technical Problem

The present disclosure is directed to providing a composition for accelerating a change in muscle type, increasing the amount of muscle, strengthening muscle, enhancing athletic ability, reducing lipids, suppressing the accumulation of lipids, lowering blood sugar, controlling body weight or lowering body weight.

Technical Solution

In one general aspect, the present disclosure provides a composition for accelerating a change in muscle type, increasing the amount of muscle, strengthening muscle, enhancing athletic ability, reducing lipids, suppressing the accumulation of lipids, lowering blood sugar, controlling body weight or lowering body weight, comprising a peroxisome proliferator-activated receptor-$\delta$ (PPAR-$\delta$) activating substance, an AMP-activated protein kinase (AMPK) activating substance and a peroxisome proliferator-activated receptor gamma coactivator 1-$\alpha$ (PGC1-$\alpha$) activating substance as an active ingredient.

Advantageous Effects

The composition according to an aspect of the present disclosure, which comprises a peroxisome proliferator-activated receptor-$\delta$ (PPAR-$\delta$) activating substance, an AMP-activated protein kinase (AMPK) activating substance and a peroxisome proliferator-activated receptor gamma coactivator 1-$\alpha$ (PGC1-$\alpha$) activating substance as an active ingredient, exhibits an effect of accelerating a change in muscle type, increasing the amount of muscle, strengthening muscle, enhancing athletic ability, reducing lipids, suppressing the accumulation of lipids, lowering blood sugar, controlling body weight or lowering body weight.

MODE FOR INVENTION

Figure 1:
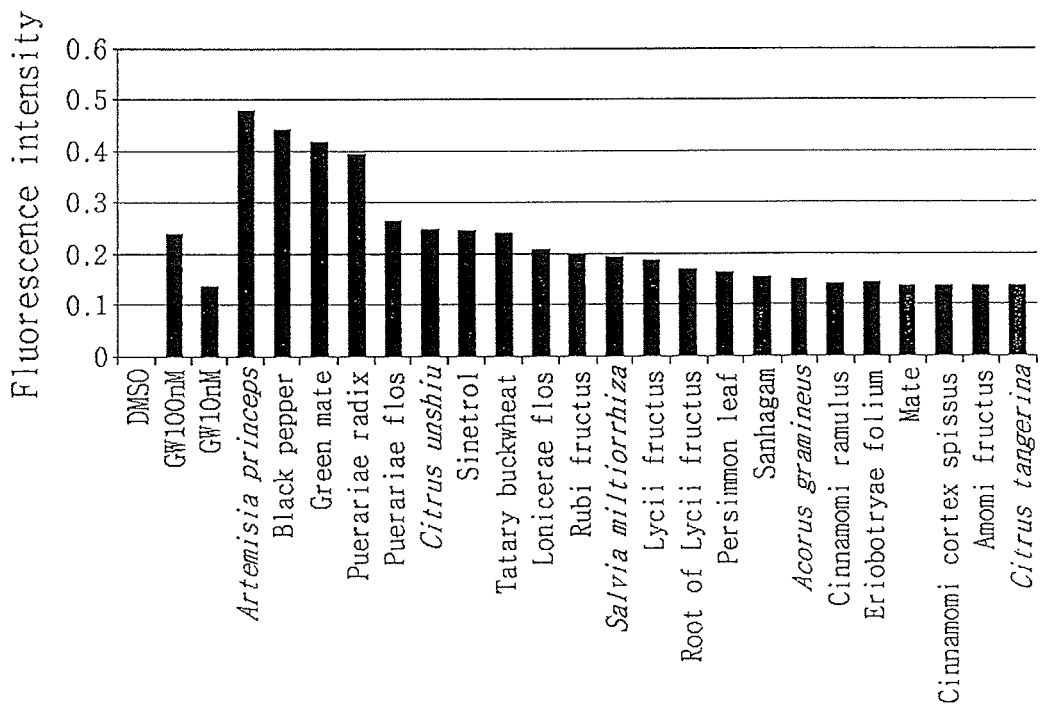
FIG. 1 shows fluorescence intensity of 22 natural product extracts as a measure of binding to LBD of PPAR-$\delta$.

As used herein, "extract" means a substance extracted from a natural product, regardless of extraction method or ingredients. The term is used in a broad sense including, for example, ingredients soluble in water or an organic solvent extracted from a natural substance using the solvent, or specific ingredients of a natural substance such as oil extracted therefrom.

As used herein, "metabolism" means the processes of breakdown of nutrients taken up by an organism, production of substances or energy required for life activities, and transport of unnecessary substances out of the body. When the metabolism occurs actively, energy consumption in the body increases.

Hereinafter, the present disclosure is described in further detail.

Peroxisome proliferator-activated receptor-δ (PPAR-δ) is a factor expressed in muscle, brown adipose tissue, etc. It is reported that adiposity is inhibited in mouse in which this transcription factor is overexpressed as a result of accelerated oxidation of fatty acids in fat cells. Also, it is known that an activator of PPAR-δ promotes metabolism of skeletal muscle cells, improves sensitivity to insulin, reduces fat cells and inhibits inflammatory response by increasing the expression of such proteins as carnitine palmitoyltransferase Iβ (CPT1β), pyruvate dehydrogenase kinase isozyme 4 (PDK4), etc.

AMP-activated protein kinase (AMPK) is a protein activated when AMP is sensed in cells. The protein protects cells from external stress by inhibiting the ATP-consuming signaling pathway and activating the ATP-synthetizing signaling pathway. It is known to inhibit fat synthesis and promote fatty acid oxidation in muscles and to suppress sugar production in the liver by inhibiting gluconeogenesis.

However, only with a substance that activates PPAR-δ and AMPK, the effect of changing muscle type from the fast-twitch type to the slow-twitch type or increasing the slow-twitch type muscle is not significant. In particular, the effect is only slight in adults whose muscles are already developed. Thus, only with a substance that activates PPAR-δ and AMPK, it is difficult to achieve the aerobic exercise effect of increasing the amount of muscle, strengthening muscle, reducing body fat, suppressing the accumulation of lipids, lowering blood sugar, controlling body weight or lowering body weight, or the like.

During aerobic exercise, the amount of mitochondria which produce energy increases in muscles. Mitochondria oxidize fatty acids and ATP is produced as the fatty acid oxidation is accelerated by mitochondria. The number and capacity of mitochondria that oxidize fatty acids are regulated by peroxisome proliferator-activated receptor gamma coactivator 1-α (PGC1-α).

In an aspect, the present disclosure provides a composition for accelerating a change in muscle type, increasing the amount of muscle, strengthening muscle, enhancing athletic ability, reducing lipids, suppressing the accumulation of lipids, lowering blood sugar, controlling body weight or lowering body weight, comprising a PPAR-δ activating substance, an AMPK activating substance and a PGC1-α activating substance as an active ingredient.

The PPAR-δ activating substance increases expression of enzymes promoting fat and sugar metabolism in muscle cells by binding to PPAR-δ and increasing its activity. The AMPK activating substance may regulate energy metabolism by accelerating phosphorylation of the AMPK protein. The PGC1-α activating substance may increase mitochondrial biosynthesis by acting on the PGC1-α promoter and promoting expression of the PGC1-α gene.

In an exemplary embodiment of the present disclosure, a composition comprising the PPAR-δ activating substance, the AMPK activating substance and the PGC1-α activating substance as an active ingredient may accelerate change in muscle type. The change in muscle type includes a change from a fast-twitch type to a slow-twitch type or an increase in the slow-twitch type. As described above, one having a large amount of slow-twitch type muscles looks slimmer even when the body weight is the same since the slow-twitch muscle has a smaller volume than the fast-twitch muscle. Further, the slow-twitch muscle reduces lipids and suppresses accumulation of the lipids in the body since it uses fats instead of carbohydrates as primary energy source. In addition, since the slow-twitch muscle is used for slow, long motion as compared to the fast-twitch muscle, the increase in slow-twitch muscle may improve endurance.

In an exemplary embodiment of the present disclosure, a composition comprising the PPAR-δ activating substance, the AMPK activating substance and the PGC1-α activating substance as an active ingredient may improve athletic ability and metabolism by increasing the amount of muscle in the body and strengthening muscle. Also, it provides the effect of reducing lipids in the body and blood and lowering blood sugar by increasing expression of the genes involved in fat and sugar metabolism in muscle cells such as CPT1β, PDK4, PGC1α, GAPDH, etc.

Accordingly, when the composition comprising the PPAR-δ activating substance, the AMPK activating substance and the PGC1-α activating substance as an active ingredient is used for an animal or human, it may provide an effect similar to that of aerobic exercise and may allow control and lowering of body weight.

In an exemplary embodiment of the present disclosure, the PPAR-δ activating substance included in the composition comprises one or more of *Artemisia princeps* extract, eicosapentaenoic acid (EPA), black pepper (*piperis nigri fuctus*) extract, green mate (*Ilex paraguariensis*) extract and puerariae radix (root of a plant in the genus *Pueraria*) extract. The EPA is a naturally-occurring PPAR-δ ligand.

In an exemplary embodiment of the present disclosure, the AMPK activating substance included in the composition comprises one or more of *Gynostemma pentaphyllum* leaf extract, *Citrus unshiu* extract and *Houttuynia cordata* extract.

In an exemplary embodiment of the present disclosure, the PGC1-α included in the composition comprises one or more of astragali radix extract, puerariae flos (flower of a plant in the genus *Pueraria*) extract and *Citrus leiocarpa* extract.

In an exemplary embodiment of the present disclosure, the extracts may be obtained by extracting the corresponding natural products according to a commonly employed method. In another exemplary embodiment of the present disclosure, the extracts may be obtained by heating and extracting the corresponding natural products in an organic solvent including water or alcohol, and then filtering and concentrating under reduced pressure. In another exemplary embodiment of the present disclosure, the organic solvent may be a $C_1$-$C_5$ low alcohol, although not being limited thereto. For example, the $C_1$-$C_5$ low alcohol may be one or more selected from a group consisting of methanol, ethanol, isopropyl alcohol, n-propyl alcohol, n-butanol and isobutanol.

In an exemplary embodiment of the present disclosure, the composition comprising the PPAR-δ activating substance, the AMPK activating substance and the PGC1-α activating substance as an active ingredient may comprise the activating substance, the AMPK activating substance and the PGC1-α activating substance in an amount of 1-80 wt % based on the total weight of the composition. In another exemplary embodiment of the present disclosure, the PPAR-δ p activating substance, the AMPK activating substance and the PGC1-α activating substance may be included in an amount of 5-60 wt % based on the total weight of the composition. In another exemplary embodiment of the present disclosure, the PPAR-δ activating substance, the AMPK activating substance and the PGC1-α activating substance may be included in an amount of 10-30 wt % based on the total weight of the composition. When the PPAR-δ activating substance, the AMPK activating substance and the PGC1-α activating substance are included in an amount of 1-80 wt % based on the total weight of the composition, the effect desired by the present disclosure can be achieved while ensuring both stability and safety of the composition and satisfying cost effectiveness.

In an exemplary embodiment of the present disclosure, in the composition comprising the PPAR-δ activating substance, the AMPK activating substance and the PGC1-α activating substance as an active ingredient, each of the PPAR-δ activating substance, the AMPK activating substance and the PGC1-α activating substance may be included in an amount of 1-30 wt % based on the total weight of the composition. In another exemplary embodiment of the present disclosure, each of the PPAR-δ activating substance, the AMPK activating substance and the PGC1-α activating substance may be included in an amount of 5-20 wt % based on the total weight of the composition. In another exemplary embodiment of the present disclosure, each of the PPAR-δ activating substance, the AMPK activating substance and the PGC1-α activating substance may be included in an amount of 5-10 wt % based on the total weight of the composition. When each of the PPAR-δ activating substance, the AMPK activating substance and the PGC1-α activating substance is included in an amount of 1-30 wt % based on the total weight of the composition, the effect desired by the present disclosure can be achieved while ensuring both stability and safety of the composition and satisfying cost effectiveness.

In an exemplary embodiment of the present disclosure, in the composition comprising the PPAR-δ activating substance, the AMPK activating substance and the PGC1-α activating substance as an active ingredient, the PPAR-δ activating substance, the AMPK activating substance and the PGC1-α activating substance may be mixed at a ratio of 1-10:1-10:1-10. In another exemplary embodiment of the present disclosure, the PPAR-δ activating substance, the AMPK activating substance and the PGC1-α activating substance may be mixed at a ratio of 1-5:1-5:1-5. In another exemplary embodiment of the present disclosure, the PPAR-δ activating substance, the AMPK activating substance and the PGC1-α activating substance may be mixed at a ratio of 1-2:1-2:1-2. When the PPAR-δ activating substance, the AMPK activating substance and the PGC1-α activating substance are mixed at the above-described ratio, the effect desired by the present disclosure can be achieved while ensuring both stability and safety of the composition and satisfying cost effectiveness.

The composition according to the present disclosure is applicable not only to animals but also to human.

In an aspect, the present disclosure provides a pharmaceutical composition comprising the PPAR-δ activating substance, the AMPK activating substance and the PGC1-α activating substance as an active ingredient.

The pharmaceutical composition may further comprise a pharmaceutical adjuvant such as antiseptic, stabilizer, hydrating agent, emulsifying accelerator, salt and/or buffer for controlling osmotic pressure, etc. or other therapeutically useful substance, and may be prepared into various formulations for oral or parenteral administration.

The formulation for oral administration may include, for example, tablet, pill, hard or soft capsule, liquid, suspension, emulsion, syrup, powder, dust, granule, pellet, or the like. These formulations may comprise, in addition to the active ingredient, a surfactant, a diluent (e.g., lactose, dextrose, sucrose, mannitol, sorbitol, cellulose or glycine) or a lubricant (e.g., silica, talc, stearic acid and magnesium or calcium salt thereof or polyethylene glycol). The tablet may comprise a binder such as magnesium aluminum silicate, starch paste, gelatin, tragacanth, methyl cellulose, sodium carboxymethyl cellulose and polyvinylpyrrolidone, and may occasionally comprise a pharmaceutical additive such as a disintegrant, e.g. starch, agar, alginic acid or a sodium salt thereof, an absorbent, a colorant, a flavor, a sweetener, or the like. The tablet may be prepared according to the commonly employed mixing, granulation or coating method.

The formulation for parenteral administration may include, for example, injection, drop, ointment, lotion, gel, cream, spray, suspension, emulsion, suppository, patch, etc., but is not limited thereto.

In an exemplary embodiment of the present disclosure, the pharmaceutical composition may be administered orally or parenterally, e.g. rectally, topically, transdermally, intravenously, intramuscularly, intraabdominally, subcutaneously, etc.

A pharmaceutically acceptable amount, i.e. administration dose, of the active ingredient will vary depending on the age, sex and body weight of the subject to be treated, particular disease or pathological condition to be treated, severity of the disease or pathological condition, administration route and discretion of the prescriber. Determination of the administration dose considering these factors is within the level of those skilled in the art. A general administration dose may be 0.01-2000 mg/kg/day, specifically 1-100 mg/kg/day. However, the described administration dose does not limit the scope of the present disclosure by any means.

In another aspect, the present disclosure provides a food composition comprising the PPAR-δ activating substance, the AMPK activating substance and the PGC1-α activating substance as an active ingredient. The food composition may be a health food composition.

The formulation of the food or health food composition is not particularly limited. For example, it may be prepared into tablet, granule, drink, caramel, diet bar, tea bag, etc. Each formulation of the food composition may comprise, in addition to the active ingredient, other ingredients commonly used in the art. Those other ingredients may be selected by those skilled in the art without difficulty by considering the particular formulation or purpose of use and may provide synergic effect.

Determination of the dose of the active ingredient is within the level of those skilled in the art. A daily dose may vary depending on various factors including the age, physical condition, complication, etc. of the subject.

In another aspect, the present disclosure provides a beauty care composition comprising the PPAR-δ activating substance, the AMPK activating substance and the PGC1-α activating substance as an active ingredient.

For example, the beauty care composition may be a cosmetic composition. The cosmetic composition may comprise a cosmetologically or dermatologically allowable medium or base. It may be provided in any topically applicable form including, for example, solution, gel, solid, anhydrous slurry, oil-in-water emulsion, water-in-oil emulsion, multiemulsion, suspension, microemulsion, microcapsule, microgranule, ionic (liposome) or non-ionic vesicular dispersion, foam, or an aerosol composition comprising a pressurized propellant. Such compositions may be prepared by a method commonly employed in the art.

The beauty care composition may further comprise fatty substance, organic solvent, solubilizer, thickening agent, gelling agent, softening agent, antioxidant, suspending agent, stabilizer, foaming agent, aromatic, surfactant, water, ionic or non-ionic emulsifier, filler, sequestrant, chelating agent, preservative, vitamin, blocker, hydrating agent, essential oil, dye, pigment, hydrophilic or lipophilic active agent, lipid vesicle or other adjuvant commonly used in the field of cosmetics or dermatology. The adjuvant is added in an amount commonly used in the field of cosmetics or dermatology.

The beauty care composition is not particularly limited with regard to the formulation thereof and the formulation may be determined appropriately depending on purposes. For example, the beauty care composition may be provided as one or more formulation selected from a group consisting of toilet water, lotion, essence, cream, ointment, gel, pack, patch, spray, powder foundation, emulsion foundation, conceal stick, hand or foot lotion, hand or foot cream, hand or foot oil, hand or foot essence, hand or foot cleanser, soap, cleansing cream, cleansing lotion, cleansing foam and cleansing water, but is not limited thereto.

The features and effects of the present disclosure will be described in detail through preparation examples, examples and test examples. However, the following preparation examples, examples and test examples are provided for illustrative purposes only and are not intended to limit the scope of the present disclosure.

PREPARATION EXAMPLE 1

Preparation of *Artemisia princeps* Extract

*Artemisia princeps* cultivated in Chengchen-dong, Jecheon-si, Chungcheongbuk-do, Korea was purchased. After adding 70% ethanol (3 L) to *Artemisia princeps* (300 g), the mixture was stirred at 70-80° C. for 3 hours. After repeating this procedure 2 times, a filtrate obtained by filtering through filter paper was concentrated under reduced pressure using a rotary vacuum evaporator, which was freeze-dried to obtain dry powder (29 g).

PREPARATION EXAMPLE 2

Preparation of *Gynostemma pentaphyllum* Leaf Extract

*Gynostemma pentaphyllum* leaf (1 kg) was crushed and repeatedly extracted 2-3 times for 12-24 hours at 90-100° C. after adding about 10 volume equivalents of water or alcohol. After filtering, the filtrate was concentrated under reduced pressure to obtain *Gynostemma pentaphyllum* leaf extract.

PREPARATION EXAMPLE 3

Preparation of Astragali Radix Extract

Astragali radix cultivated in Korea was purchased from a local market. Astragali radix and triply distilled water were mixed at a ratio of 1:10 and extraction was performed for 3 hours using an extractor. After repeating this procedure 2 times, a filtrate obtained by filtering through filter paper was concentrated under reduced pressure using a rotary vacuum evaporator, which was freeze-dried to obtain astragali radix extract as dry powder.

EXAMPLES

The *Artemisia princeps* extract, the *Gynostemma pentaphyllum* leaf extract and the astragali radix extract prepared above were mixed at a ratio of 1:1:1 (Example 1). Also, EPA, the *Gynostemma pentaphyllum* leaf extract and the astragali radix extract were mixed at a ratio of 1:1:1 (Example 2).

Test Example 1

Screening of PPAR-δ Activating Substance

Peroxisome proliferator-activated receptor-δ (PPAR-δ) is activated when a ligand binds to the ligand binding domain (LBD) of the protein and regulates expression of other genes. Accordingly, a substance should easily bind to the LBD to activate the transcription factor. Based on this fact, about 90 edible natural products were screened for PPAR-δ activating substance.

The natural products were dissolved in dimethyl sulfoxide (DMSO) to 200, 100 or 50 μg/mL and the degree of binding to the LBD of PPAR-δ was quantified with fluorescence intensity using the LanthaScreen TR-FRET peroxisome proliferator receptor delta coactivator assay kit (Invitrogen, CA). DMSO was used as negative control. The result for the 22 natural products that showed superior binding to the LBD of PPAR-δ is shown in FIG. 1.

As seen from FIG. 1, *Artemisia princeps*, black pepper, green mate and puerariae radix showed superior activity among them. In particular, *Artemisia princeps* had an $EC_{50}$ value for the LBD of PPAR-δ ligand of 9 μg/mL.

Test Example 2

Screening of AMPK Activating Substance

About 90 edible natural products were screened for AMP-activated protein kinase (AMPK) activating effect as follows.

Immature C2C12 cells were purchased from the American Tissue Culture Collection (ATCC; USA). The cells were cultured in Dulbecco's modified Eagle's Medium (DMEM; Gibco 1210-0038) containing 10% fetal bovine serum (FBS) in a 5% $CO_2$ incubator until 70% confluency while replacing the medium every other day. The cells were induced to differentiate into muscle cells in a medium containing 2% horse serum (HS). After culturing for 4 days in a medium containing 2% HS, the muscle cells were treated with the natural products dissolved in DMSO (200 μg/mL) for 24 hours.

As positive control, 1 mL of AICAR (Cell Signaling Technology, Inc., UK) which is well known as AMPK activator was used. As negative control, DMSO of a volume of 1/1000 as that of the medium was used. 24 hours later, the cells were washed with phosphate buffered saline (PBS), treated with 200 μL of a protein extraction buffer containing 8 M urea, 2% 3-[(3-chloramidopropyl)-dimethylammonio]-1-propane-sulfonate (CHAPS), 50 mM dithiothreitol (DTT), 2 M thiourea, 2 mM phenylmethanesulfonyl fluoride (PMSF) and 100 μg/μL leupeptin, and then kept at room temperature for 10 minutes. Subsequently, after centrifugation at 4° C. and 15,000 g for 10 minutes and collecting the supernatant, protein was quantitated using Bio-Rad Protein Dye Reagent™. 100 g of protein was separated based on size with 8% SDS-PAGE and blotted onto PDF membrane (Bio-Rad) at 50 V for 12 hours. The blots obtained were blocked with 5% skim milk for 1 hour, reacted with anti-AMPK-α (Cell signaling), anti-phospho-AMPK-α (Cell Signaling) and anti-6-actin as primary antibody and with a secondary antibody conjugated with horse radish peroxidase (Amersham Biosciences), and detected using the enhanced chemiluminescence (ECL) kit (Amersham Biosciences). The reacted blots were exposed to Fuji X-ray film and developed to identify the degree of protein expression. Bands on the film were scanned with PowerLook 2100 XL (UMAX) and analyzed using the ImageMaster 2D Elite program (Amersham Bioscience).

Figure 2:
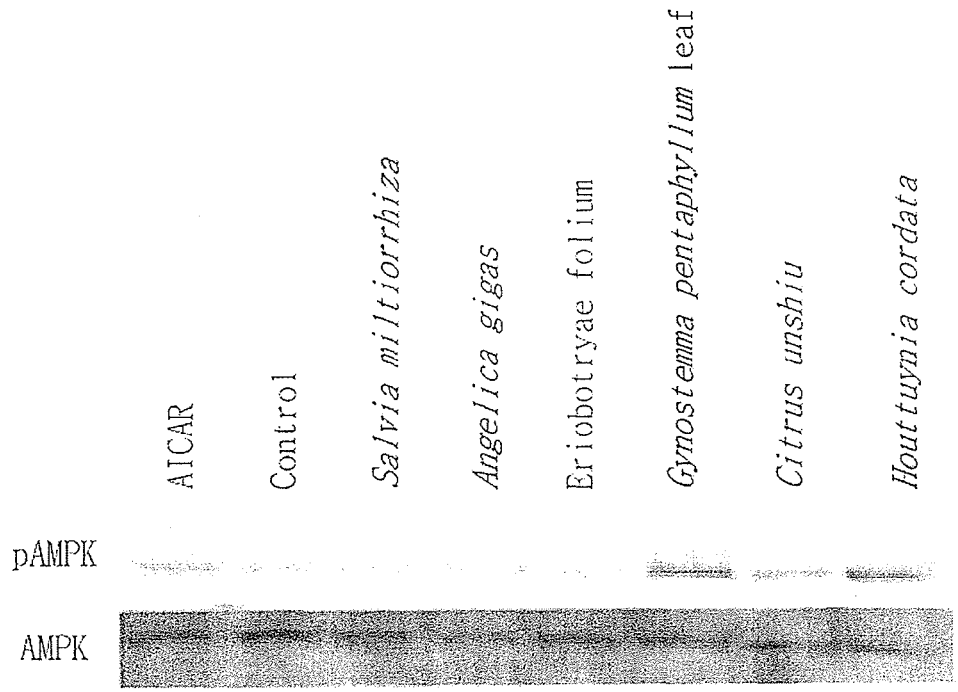
FIG. 2 shows the level of AMPK phosphorylation when muscle cells were treated for 24 hours with *Salvia miltiorrhiza*, *Angelica gigas*, eriobotryae folium, *Gynostemma pentaphyllum* leaf, *Citrus unshiu* or *Houttuynia cordata* extract.

The result for 6 plants that exhibited superior AMPK activating effect among the tested natural products is shown in FIG. 2. From FIG. 2, it can be seen that the cells treated with *Gynostemma pentaphyllum* leaf, *Citrus unshiu* and *Houttuynia cordata* show remarkably increased AMPK phosphorylation.

Test Example 3

Screening of PGC1-α Activating Substance

APRDC PGC1-α promoter cells were used to test PGC1-α promoter activating effect of 90 natural products. The APRDC PGC1-α promoter cells are human hepatic cells (KCTC 11218BP) in which a vector with the PGC1-α promoter and the luciferase gene genetically fused is stably expressed.

First, APRDC PGC1-α promoter cells were treated with the 90 natural products dissolved in DMSO (200 μg/mL) for 24 hours. Then, after washing 2 times with PBS, the activity of the reporter gene luciferase was measured using the Steady Glo luciferase assay kit (Promega, Cat No. E2520). The luciferase activity was measured by transferring the sample to a 96-well plate and detecting fluorescence using a luminometer. DMSO was used as negative control.

Figure 3:
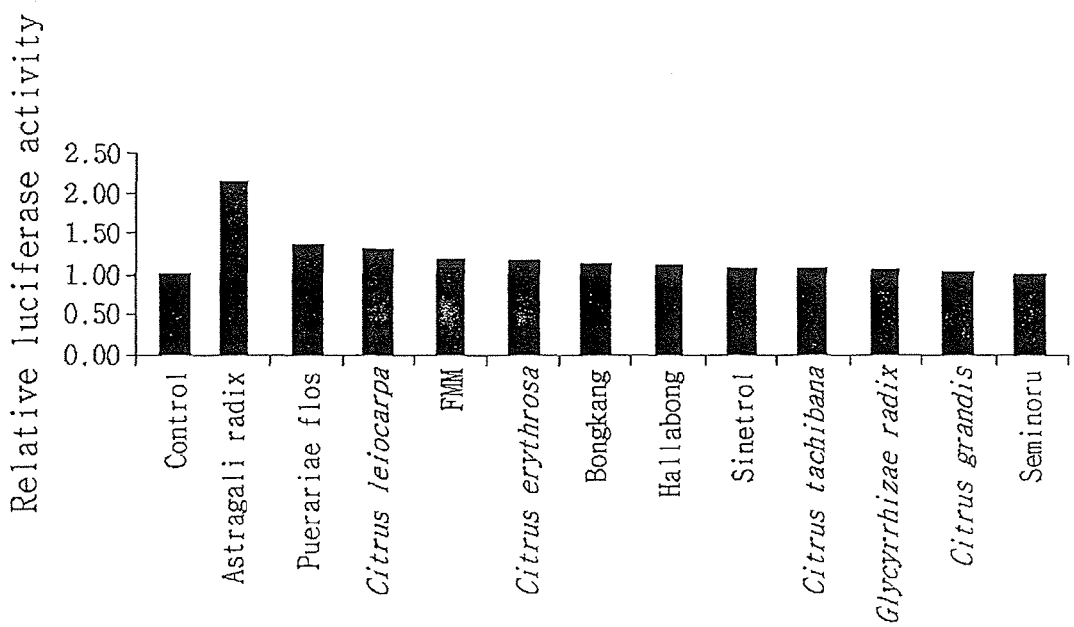
FIG. 3 shows the level of luciferase expression as a result of activation of the PGC1-$\alpha$ activating substance by several natural product extracts including astragali radix extract.

The result for several natural products that exhibited superior APRDC PGC1-α promoter activating effect among the tested natural products is shown in FIG. 3. As seen from FIG. 3, treatment with astragali radix, puerariae flos or *Citrus leiocarpa* resulted in stronger fluorescence as compared to the negative control DMSO or other substances. This means that astragali radix, puerariae flos and *Citrus leiocarpa* have superior PGC1-α promoter activating effect.

Test Example 4

Evaluation of Gene Expression in Muscle Cells (at Cellular Level)

The effect of treatment with a 1:1:1 mixture of the *Artemisia princeps* extract, the *Gynostemma pentaphyllum* leaf extract and the astragali radix extract, which were confirmed to activate PPAR-δ, AMPK and PGC1-α, on the expression of the genes involved in fat and sugar metabolism in muscle cells was investigated.

Immature C2C12 muscles were purchased from the ATCC (USA). The cells were cultured in DMEM (Gibco 1210-0038) containing 10% FBS in a 5% $CO_2$ incubator until 70% confluency while replacing the medium every other day. The cells were induced to differentiate into muscle cells in a medium containing 2% HS. After culturing for 4 days in a medium containing 2% HS, the muscle cells were treated with the *Artemisia princeps* extract, the *Gynostemma pentaphyllum* leaf extract, the astragali radix extract or mixtures thereof (200 μg/mL). As negative control, DMSO of a volume of 1/1000 as that of the medium was used. After culturing the cells treated with each sample for 24 hours at 37° C. and washing 2 times with cold saline, RNA was extracted using the TRIzol reagent (Invitrogen). cDNA was synthesized using the extracted and quantitated RNA (1 μg/μL) and a reverse transcription system (Promega).

Expression profile of the CPT1β, PDK4, PGC1α and GAPDH genes was measured using the synthesized cDNA and primers and probes (Applied Biosystems; CPT1β, Mm00487200_m1; PDK4, Mm00447181_m1; PGC1-α Mm00447181_m1; GAPDH, Mm99999915_q1) designed for the genes. PCR and analysis were performed using the Rotor-Gene 3000 system (Corbett Research, Sydney, Australia). The result is shown in FIG. 4.

Figure 4:
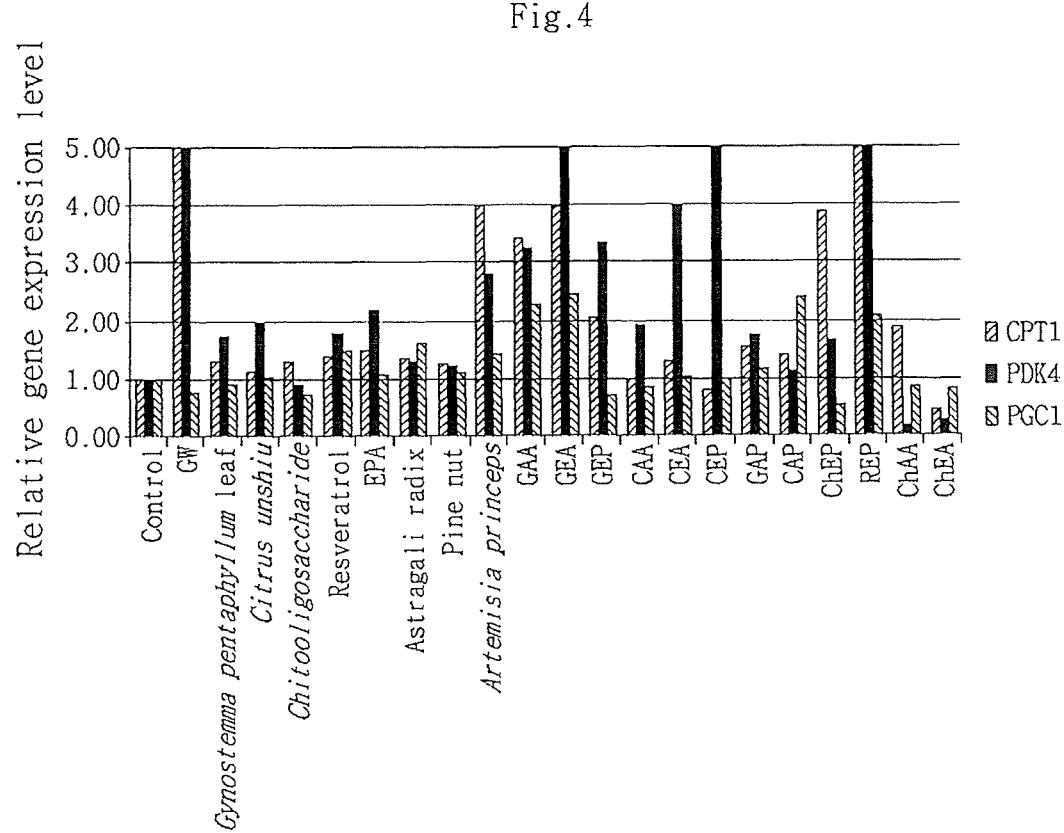
FIG. 4 shows a result of treating muscle cells with various substances including 200 μg/mL *Artemisia princeps* extract, EPA, *Gynostemma pentaphyllum* leaf extract, astragali radix extract or mixtures thereof and comparing expression level of the CPT1$\beta$, PDK4 and PGC1-$\alpha$ genes with a negative control group (GAA: *Gynostemma pentaphyllum* leaf extract+*Artemisia princeps* extract+astragali radix extract, GEA: *Gynostemma pentaphyllum* leaf extract+EPA+astragali radix extract, GEP: *Gynostemma pentaphyllum* leaf extract+EPA+pinotin (pine nut extract), CAA: *Citrus unshiu* extract+*Artemisia princeps* extract+astragali radix extract, CEA: *Citrus unshiu* extract+EPA+astragali radix extract, CEP: *Citrus unshiu* extract+EPA+pinotin (pine nut extract), GAP: *Gynostemma pentaphyllum* leaf extract+*Artemisia princeps* extract+pinotin (pine nut extract), CAP: *Citrus unshiu* extract+*Artemisia princeps* extract+pinotin (pine nut extract), ChEP: chitooligosaccharide+EPA+pinotin (pine nut extract), REP: resveratrol+EPA+pinotin (pine nut extract), ChAA: chitooligosaccharide+*Artemisia princeps* extract+astragali radix extract, ChEA: chitooligosaccharide+EPA+astragali radix extract).

As seen from FIG. 4, treatment with the mixture of the three substances increased the expression of the CPT1β, PDK4 and PGC1-α genes 2 times or more as compared to when the negative control substance was used or the substance was used alone. Accordingly, it can be seen that administration of a mixture of the substances that activate the PPAR-δ, AMPK and PGC1-α respectively can promote fat and sugar metabolism in muscle.

Test Example 5

Evaluation of Exercise Duration (1) Preparation of Experimental Mouse 5-week-old male C57BL/6 mice were divided into a normal diet group, a high-fat diet group and an aerobic exercise group, with 10 mice per group. The normal diet group was fed with D12450B (10% fat, Research Diets, Inc., NJ, USA) and the high-fat diet group was fed with D12492 (60% fat) for 8 weeks. The aerobic exercise group was given the high-fat diet and made to run on a treadmill for 40 minutes at 15 m/min, 5 times a week. The test groups were given the high-fat diet and orally administered with *Gynostemma pentaphyllum* leaf extract, *Artemisia princeps* extract, astragali radix extract, EPA, a mixture of *Artemisia princeps* extract, *Gynostemma pentaphyllum* leaf extract and astragali radix extract or a mixture of EPA, *Gynostemma pentaphyllum* leaf extract and astragali radix extract (200 mg/kg) once a day. Body weight and feed intake were measured every week.

Figure 5:
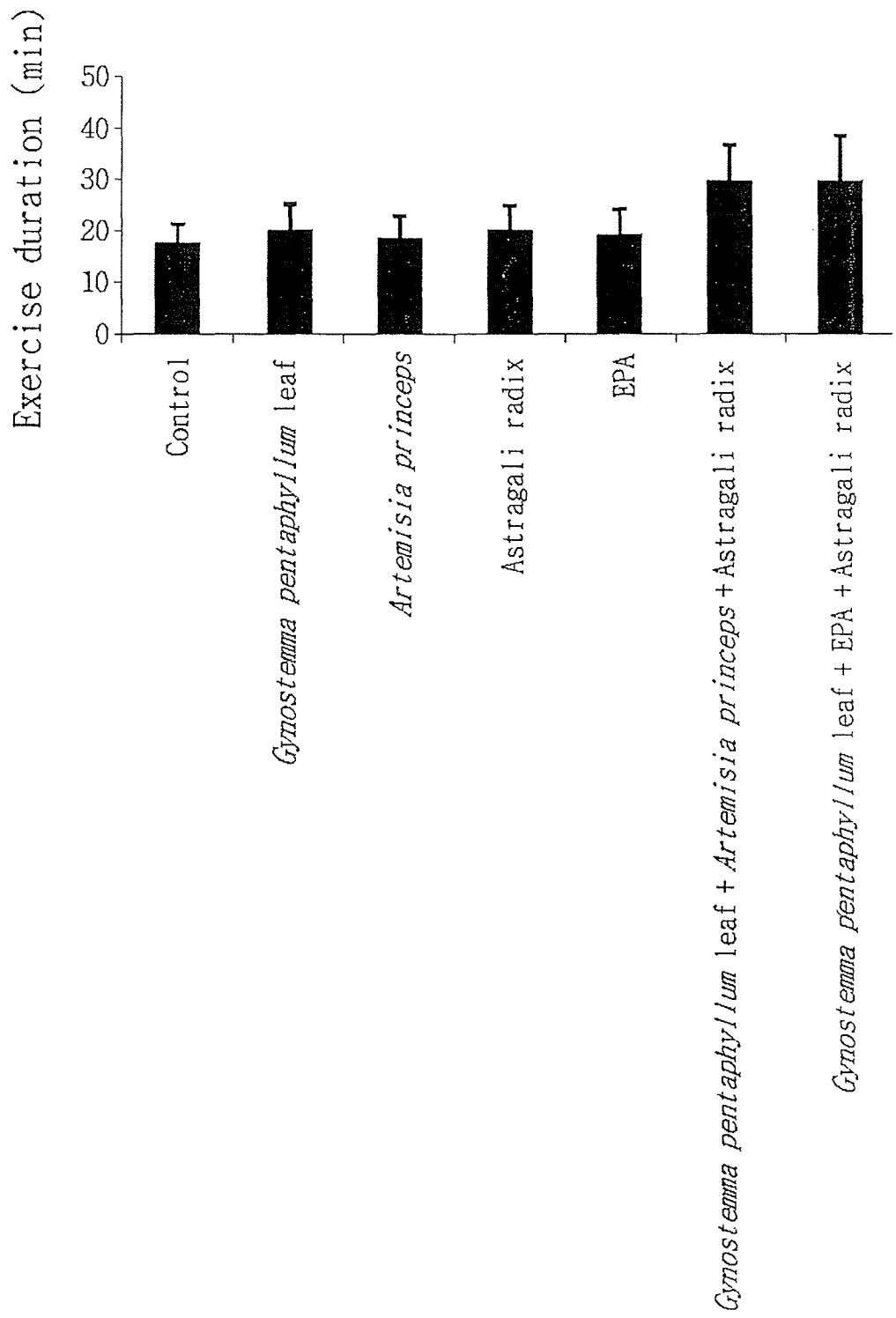
FIG. 5 shows exercise duration of groups to which *Artemisia princeps* extract, EPA, *Gynostemma pentaphyllum* leaf extract, astragali radix extract or mixtures thereof were administered.

(2) Measurement of Exercise Duration 8 weeks after the administration of the test substances, the experimental mice were forced to run on a treadmill at 15 m/min and exercise duration was measured. The result is shown in FIG. 5. As seen from FIG. 5, the group to which the mixture of *Gynostemma pentaphyllum* leaf extract, *Artemisia princeps* extract and astragali radix extract or the mixture of *Gynostemma pentaphyllum* leaf extract, EPA and astragali radix extract was administered showed about 70% increased exercise duration as compared to the untreated negative control group or the groups to which the test substances were administered alone.

Accordingly, it can be seen that administration of a mixture of the substances that activate PPAR-δ, AMPK and PGC1-α respectively enables exercise for a long time.

Test Example 6

Measurement of Body Weight and Tissue Weight 5-week-old male C57BL/6 mice were grouped with 10 mice per group. They were orally administered with *Gynostemma pentaphyllum* leaf extract, *Artemisia princeps* extract, astragali radix extract or EPA alone, a mixture of *Artemisia princeps* extract, *Gynostemma pentaphyllum* leaf extract and astragali radix extract or a mixture of EPA, *Gynostemma pentaphyllum* leaf extract and astragali radix extract (200 mg/kg) as test substances once a day. The experimental mice were fasted for 12 hours before autopsy.

Figure 6:
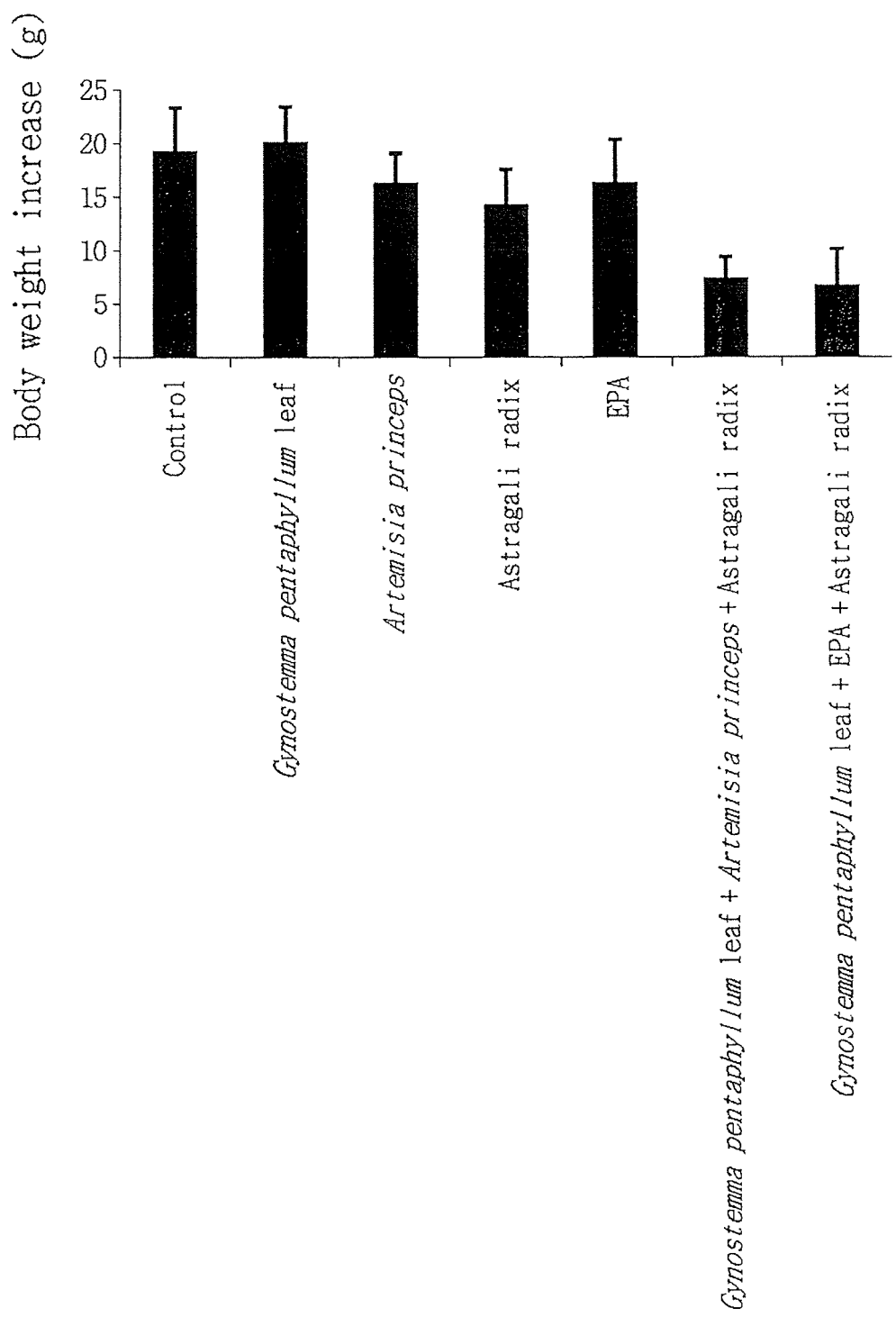
FIG. 6 shows body weight increase of groups to which *Artemisia princeps* extract, EPA, *Gynostemma pentaphyllum* leaf extract, astragali radix extract or mixtures thereof were administered.

FIG. 6 shows change in body weight for 8 weeks. As seen from FIG. 6, the group to which the mixture of *Gynostemma pentaphyllum* leaf extract, *Artemisia princeps* extract and astragali radix extract and the group to which the mixture of *Gynostemma pentaphyllum* leaf extract, EPA and astragali radix extract was administered showed 26% and 28% decreased body weight, respectively, as compared to the untreated negative control group or the groups to which the test substances were administered alone.

Figure 7:
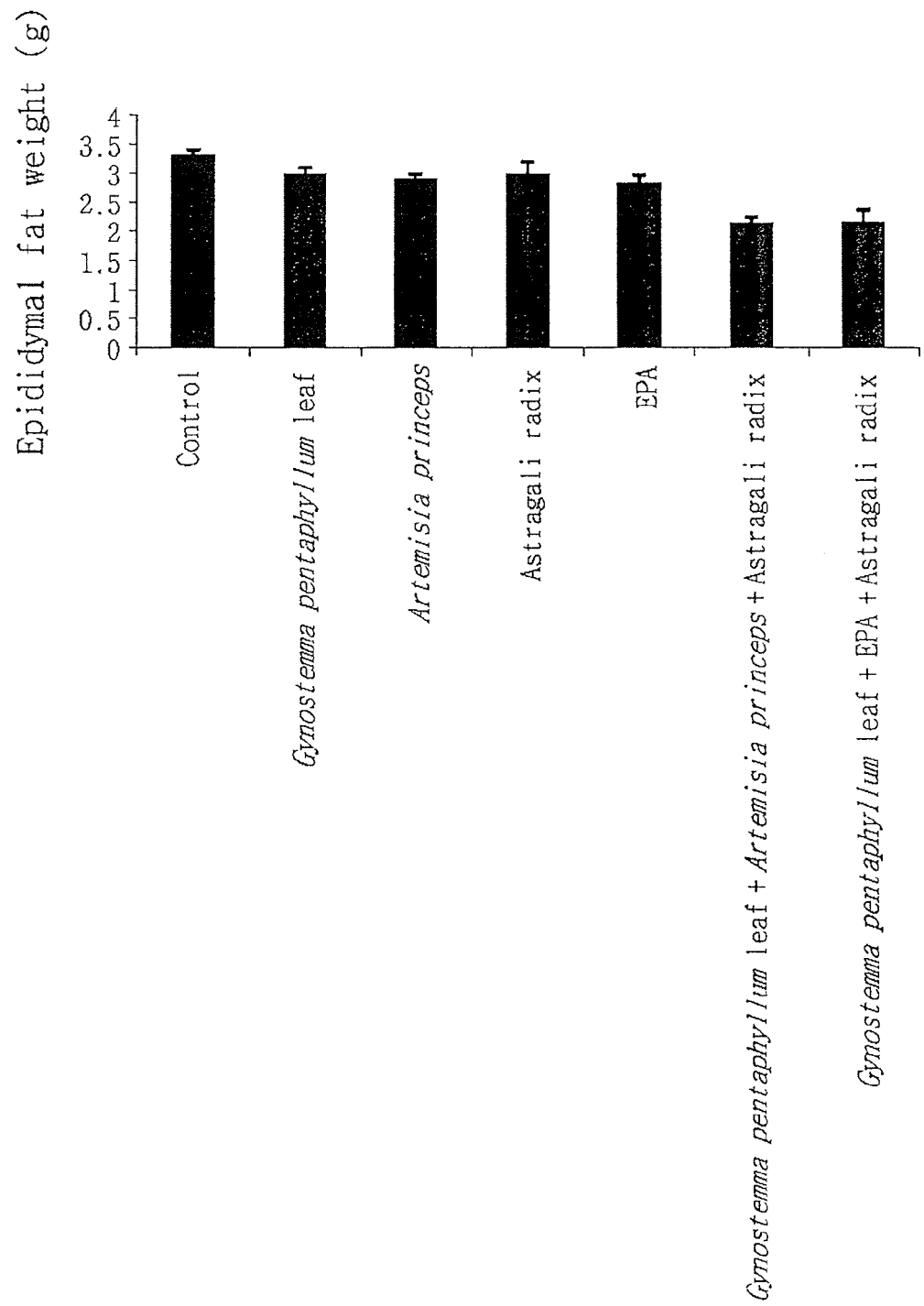
FIG. 7 shows epididymal fat weight of groups to which *Artemisia princeps* extract, EPA, *Gynostemma pentaphyllum* leaf extract, astragali radix extract or mixtures thereof were administered.

Epididymal fat weight is shown in FIG. 7. As seen from FIG. 7, the weight decreased in the group to which the mixture of *Gynostemma pentaphyllum* leaf extract, *Artemisia princeps* extract and astragali radix extract and the group to which the mixture of *Gynostemma pentaphyllum* leaf extract, EPA and astragali radix extract was administered by 34% and 36%, respectively, as compared to the untreated negative control group or the groups to which the test substances were administered alone.

Figure 8:
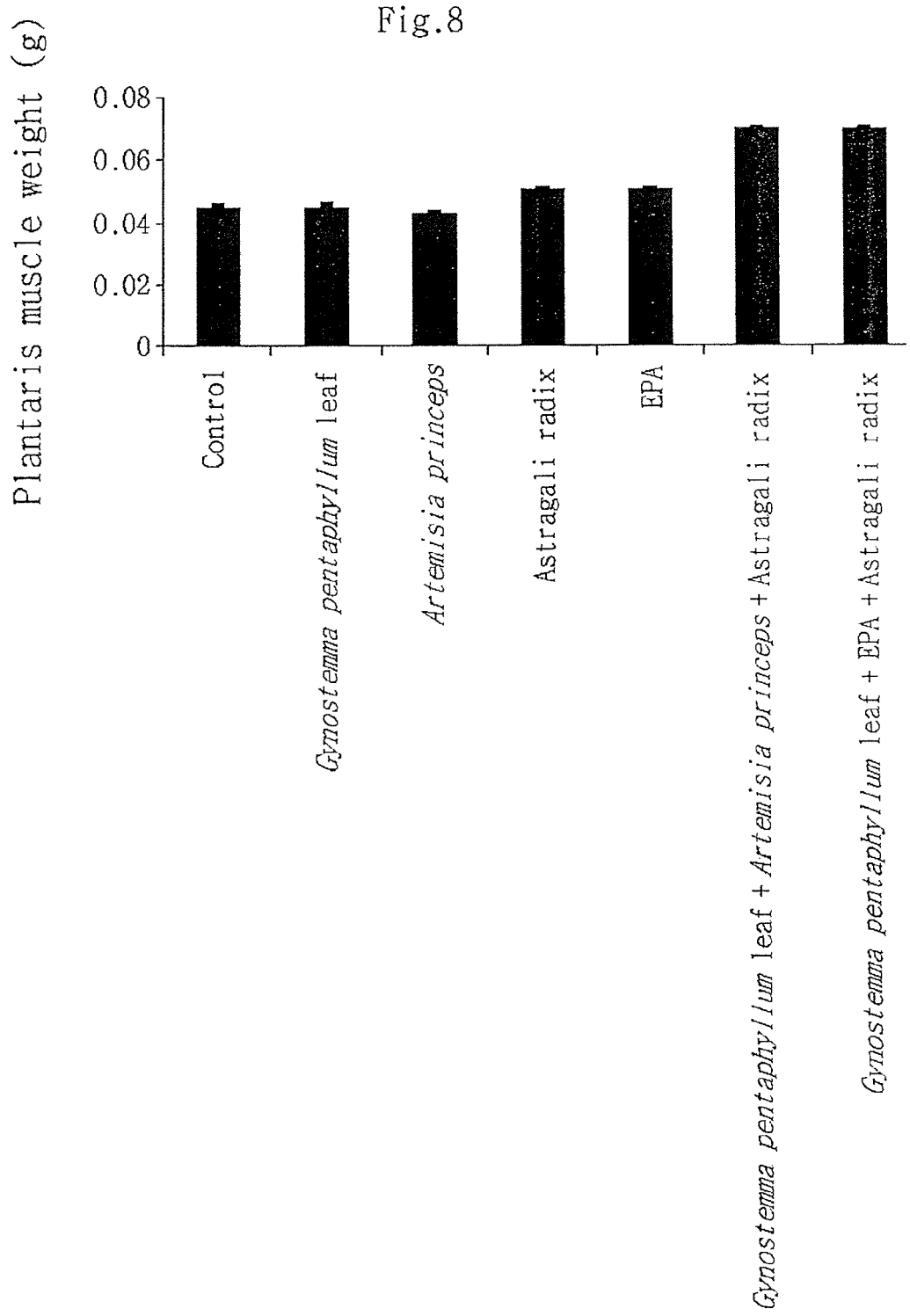
FIG. 8 shows plantaris muscle weight of groups to which *Artemisia princeps* extract, EPA, *Gynostemma pentaphyllum* leaf extract, astragali radix extract or mixtures thereof were administered.

The result of separating and weighing the mouse plantaris muscle is shown in FIG. 8. As seen from FIG. 8, the plantaris muscle weight increased in the group to which the mixture of *Gynostemma pentaphyllum* leaf extract, *Artemisia princeps* extract and astragali radix extract and the group to which the mixture of *Gynostemma pentaphyllum* leaf extract, EPA and astragali radix extract was administered by about 55% as compared to the untreated negative control group or the groups to which the test substances were administered alone.

Accordingly, it can be seen that administration of a mixture of the substances that activate PPAR-δ, AMPK and PGC1-α respectively increases the amount of muscle while lowering body weight and epididymal fat weight.

Test Example 7

Blood Analysis 5-week-old male C57BL/6 mice were grouped with 10 mice per group. They were orally administered with *Gynostemma pentaphyllum* leaf extract, *Artemisia princeps* extract, astragali radix extract or EPA alone, a mixture of *Artemisia princeps* extract, *Gynostemma pentaphyllum* leaf extract and astragali radix extract or a mixture of EPA, *Gynostemma pentaphyllum* leaf extract and astragali radix extract (200 mg/kg) as test substances for 8 weeks, once a day. Then, blood analysis was performed to evaluate blood sugar level and serum triglyceride and cholesterol levels.

The blood sugar level was measured using the Accu-Check Active kit (Roche Diagnostics, Seoul, Korea).

The blood sample was centrifuged at 3000 rpm for 10 minutes to separate serum. Triglyceride and cholesterol levels in the separated serum were analyzed using the Vitalab Selectra E analyzer (Vital Scientific, Dieren, The Netherlands). The result is shown in Table 1.

TABLE 1

| Group | Blood sugar (mg/dL) | Triglyceride (mg/dL) | Cholesterol (mg/dL) |
|---|---|---|---|
| Control | 183.5 ± 9.1 | 100.4 ± 8.7 | 160.2 ± 5.33 |
| *Gynostemma pentaphyllum* leaf extract | 180.2 ± 8.47 | 102.98 ± 9.7 | 167.4 ± 9.7 |
| *Artemisia priceps* extract | 176.3 ± 10.1 | 99.34 ± 5.4 | 170.3 ± 11.2 |
| Astragali radix extract | 179.9 ± 8.92 | 89.74 ± 5.4 | 159.3 ± 4.5 |
| EPA | 181.2 ± 10.9 | 101.23 ± 11.3 | 164.9 ± 12.1 |
| *Gynostemma pentaphyllum* leaf extract + *Artemisia priceps* extract + astragali radix extract | 169.3 ± 8.6 | 62.5 ± 8.5 | 175.34 ± 10.23 |
| *Gynostemma pentaphyllum* leaf extract + EPA + astragali radix extract | 169.6 ± 6.5 | 80.8 ± 8.3 | 156.2 ± 5.4 |

As seen from Table 1, the group to which the mixture of *Gynostemma pentaphyllum* leaf extract, *Artemisia princeps* extract and astragali radix extract or the mixture of *Gynostemma pentaphyllum* leaf extract, EPA and astragali radix extract was administered showed significantly lower blood sugar and triglyceride levels as compared to the untreated negative control group or the groups to which the test substances were administered alone.

Accordingly, it can be seen that administration of a mixture of the substances that activate PPAR-δ, AMPK and PGC1-α respectively provides the effect of lowering blood sugar and triglyceride levels.

Test Example 8

Analysis of Adiponectin and Insulin Levels 5-week-old male C57BL/6 mice were grouped with 10 mice per group. They were orally administered with *Gynostemma pentaphyllum* leaf extract, *Artemisia princeps* extract, astragali radix extract or EPA alone, a mixture of *Artemisia princeps* extract, *Gynostemma pentaphyllum* leaf extract and astragali radix extract or a mixture of EPA, *Gynostemma pentaphyllum* leaf extract and astragali radix extract (200 mg/kg) as test substances for 8 weeks, once a day. Then, adiponectin and insulin levels were measured.

Figure 9:
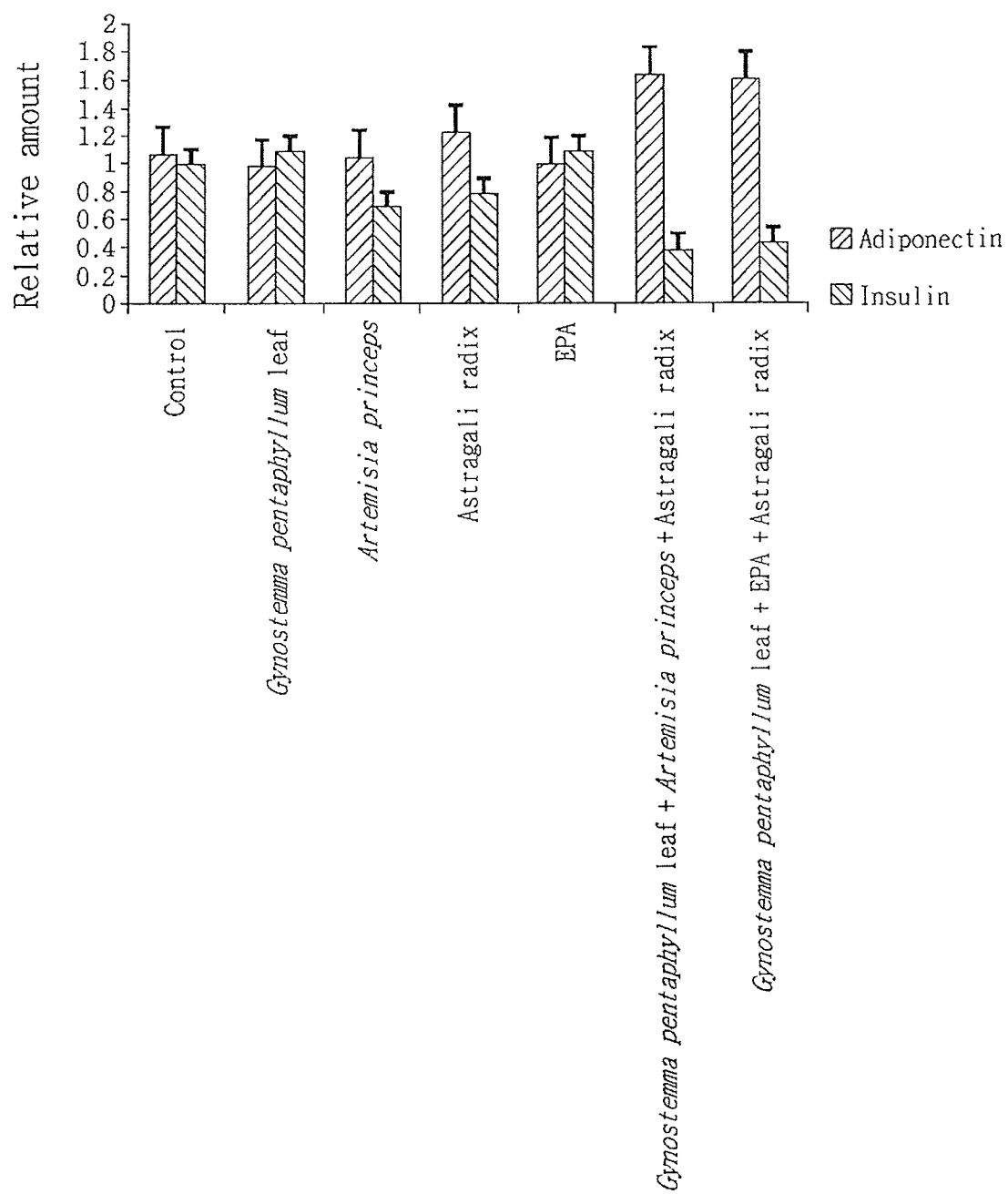
FIG. 9 compares the amount of adiponectin and insulin in groups to which *Artemisia princeps* extract, EPA, *Gynostemma pentaphyllum* leaf extract, astragali radix extract or mixtures thereof were administered relative to a negative control.

Blood was taken in an anticoagulant tube and centrifuged at 3000 rpm for 10 minutes to separate serum. The serum was diluted 20,000 times and the quantity of expressed adiponectin was measured using the Mouse Adiponectin Quantikine kit (R&D Systems). Insulin level was measured using the Mouse Insulin Quantikine kit (R&D Systems) after diluting the serum 20,000 times. The result is shown in FIG. 9.

The group to which the mixture of *Gynostemma pentaphyllum* leaf extract, *Artemisia princeps* extract and astragali radix extract or the mixture of *Gynostemma pentaphyllum* leaf extract, EPA and astragali radix extract was administered showed about 50% increased adiponectin level as compared to the untreated negative control group or the groups to which the test substances were administered alone. Also, the group to which the mixture of *Gynostemma pentaphyllum* leaf extract, *Artemisia princeps* extract and astragali radix extract and the group to the mixture of *Gynostemma pentaphyllum* leaf extract, EPA and astragali radix extract was administered showed 60% and 55% decreased insulin level, respectively, as compared to the untreated negative control group or the groups to which the test substances were administered alone.

Accordingly, it can be seen that administration of a mixture of the substances that activate PPAR-δ, AMPK and PGC1-α respectively may increase the level of the protein hormone adiponectin, which is involved in the regulation of blood sugar and fatty acid metabolism, and decrease insulin level. Decreased insulin level means that blood sugar is maintained low.

Test Example 9

Analysis of Change in Muscle Type 5-week-old male C57BL/6 mice were grouped with 10 mice per group to evaluate change in muscle type after administration of test substances. The experimental mice were orally administered with *Gynostemma pentaphyllum* leaf extract, *Artemisia princeps* extract, astragali radix extract or EPA alone, a mixture of *Artemisia princeps* extract, *Gynostemma pentaphyllum* leaf extract and astragali radix extract or a mixture of EPA, *Gynostemma pentaphyllum* leaf extract and astragali radix extract (200 mg/kg) as test substances for 8 weeks, once a day. The mice were fasted for 12 hours before autopsy.

Plantaris muscle was taken from the mice of each test group and frozen in liquid nitrogen. The frozen tissue was sliced to 10-μm thickness using a cryotome, fixed in acetone for 10 minutes, and washed 3 times with PBS. After blocking for 2 hours with PBS containing 10% FBS, the tissue sections were treated with anti-slow-twitch myosin antibody (Abcam, Cambridge, UK) as primary antibody and with fluorescein isothiocyanate (FITC)-conjugated anti-mouse IgG antibody (Molecular Probes) as secondary antibody. After mounting with antifade solution, the sections were examined by confocal microscopy.

Figure 10:
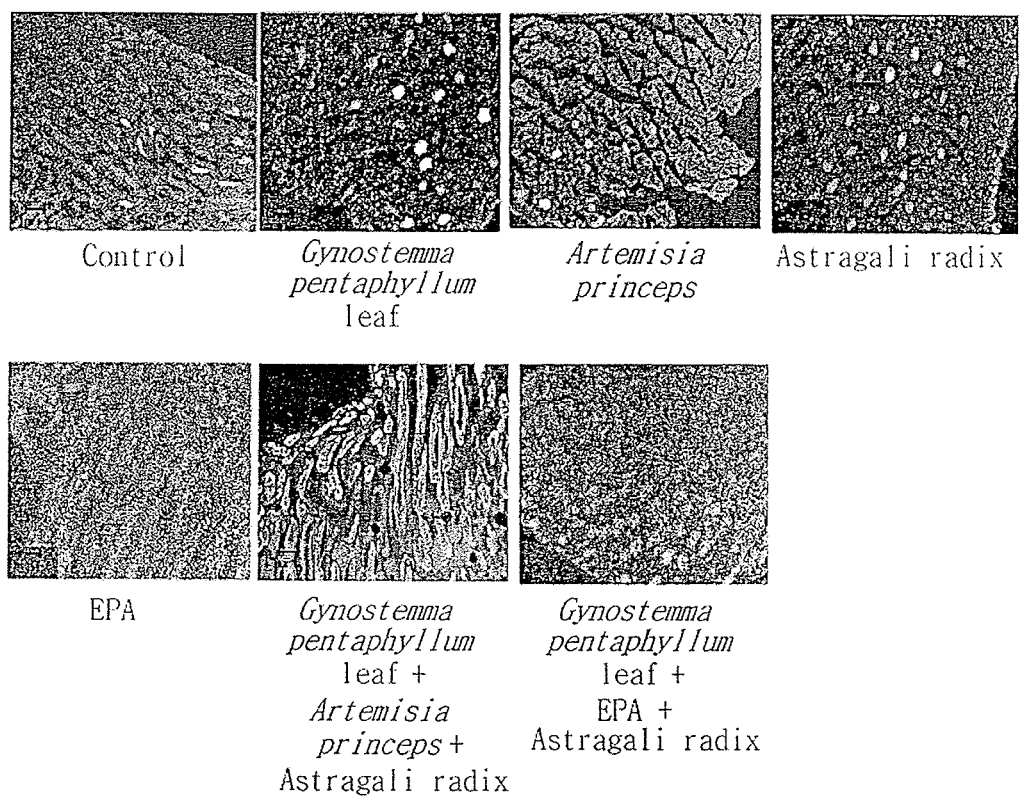
FIG. 10 shows muscle type of groups to which *Artemisia princeps* extract, EPA, *Gynostemma pentaphyllum* leaf extract, astragali radix extract or mixtures thereof were administered.

The analysis result is shown in FIG. 10 and Table 2.

TABLE 2

| Group | Slow-twitch muscle (%) | Fast-twitch muscle (%) |
|---|---|---|
| Control | 25.4 ± 1.6 | 74.5 ± 2.6 |
| *Gynostemma pentaphyllum* leaf extract | 30.6 ± 2.1 | 69.4 ± 3.1 |
| *Artemisia priceps* extract | 24.3 ± 2.7 | 75.7 ± 3.76 |

TABLE 2-continued

| Group | Slow-twitch muscle (%) | Fast-twitch muscle (%) |
|---|---|---|
| Astragali radix extract | 24.5 ± 1.9 | 75.5 ± 3.1 |
| EPA | 29.4 ± 4.2 | 70.6 ± 3.6 |
| *Gynostemma pentaphyllum* leaf extract + *Artemisia priceps* extract + astragali radix extract | 49.5 ± 3.4 | 44.3 ± 4.3 |
| *Gynostemma pentaphyllum* leaf extract + EPA + astragali radix extract | 50.4 ± 4.3 | 55.6 ± 4.3 |

The group to which the mixture of *Gynostemma pentaphyllum* leaf extract, *Artemisia princeps* extract and astragali radix extract or the mixture of *Gynostemma pentaphyllum* leaf extract, EPA and astragali radix extract was administered showed about 2 times increased slow-twitch myosin in the muscle tissue as compared to the untreated negative control group or the groups to which the test substances were administered alone. This means that administration of the mixture of *Gynostemma pentaphyllum* leaf extract, *Artemisia princeps* extract and astragali radix extract or the mixture of *Gynostemma pentaphyllum* leaf extract, EPA and astragali radix extract changes mouse muscle type to the slow-twitch muscle. Also, this means that administration of a mixture of the substances that activate PPAR-δ, AMPK and PGC1-α respectively may provide a similar effect as that of aerobic exercise in terms of change in muscle type.

Test Example 10

Analysis of Triglyceride in Hepatic Tissue 5-week-old male C57BL/6 mice were grouped with 10 mice per group. The experimental mice were orally administered with *Gynostemma pentaphyllum* leaf extract, *Artemisia princeps* extract, astragali radix extract or EPA alone, a mixture of *Artemisia princeps* extract, *Gynostemma pentaphyllum* leaf extract and astragali radix extract or a mixture of EPA, *Gynostemma pentaphyllum* leaf extract and astragali radix extract (200 mg/kg) as test substances for 8 weeks, once a day, and then triglyceride level in hepatic tissue was evaluated. The mice were fasted for 12 hours before autopsy.

Hepatic tissue was taken from the experimental mice and frozen in liquid nitrogen. The frozen tissue was sliced to 10-μm thickness using a cryotome, reacted with 0.5% Oil Red 0 (0-0625, Sigma-Aldrich, USA) in propylene glycol (031301, Samchun pure chemical Co. Ltd., Korea) for 8 minutes at 60° C., and then reacted for 2 minutes with 85% propylene glycol. Thereafter, the tissue sections were washed for 1 minute with flowing water, counter-stained with Mayer's hematoxylin (10029273, DAKO, USA), and observed under an optical microscope. The result is shown in FIG. 11.

Figure 11:
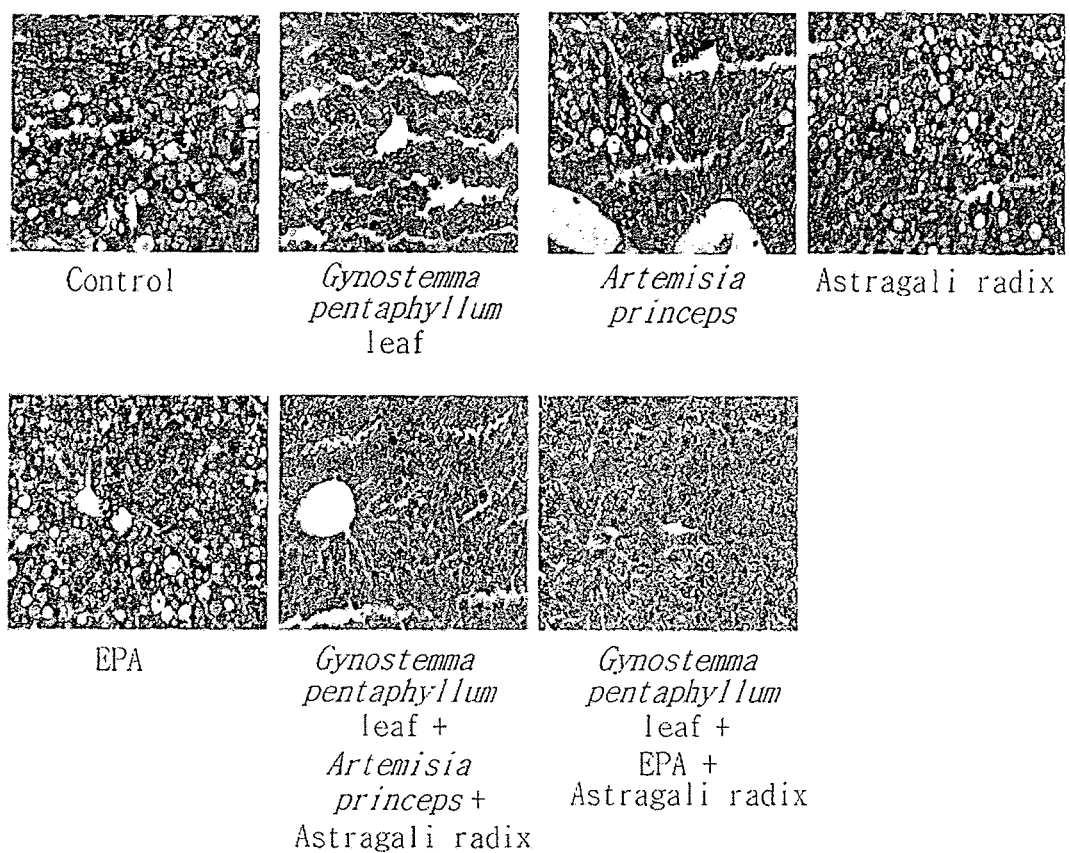
FIG. 11 shows hepatic triglyceride level of groups to which *Artemisia princeps* extract, EPA, *Gynostemma pentaphyllum* leaf extract, astragali radix extract or mixtures thereof were administered.

As seen from FIG. 11, the group to which the mixture of *Gynostemma pentaphyllum* leaf extract, *Artemisia princeps* extract and astragali radix extract or the mixture of *Gynostemma pentaphyllum* leaf extract, EPA and astragali radix extract was administered looks lighter as compared to the untreated negative control group or the groups to which the test substances were administered alone, suggesting that triglycerides are remarkably decreased in hepatic tissue.

Accordingly, it can be seen that administration of a mixture of the substances that activate PPAR-δ, AMPK and PGC1-α respectively may reduce triglycerides in hepatic tissue.

Test Example 11

Analysis of Lipid Droplets in Brown Adipose Tissue 5-week-old male C57BL/6 mice were grouped with 10 mice per group. The experimental mice were orally administered with *Gynostemma pentaphyllum* leaf extract, *Artemisia princeps* extract, astragali radix extract or EPA alone, a mixture of *Artemisia princeps* extract, *Gynostemma pentaphyllum* leaf extract and astragali radix extract or a mixture of EPA, *Gynostemma pentaphyllum* leaf extract and astragali radix extract (200 mg/kg) as test substances for 8 weeks, once a day, and then lipid droplets in brown adipose tissue was examined. The mice were fasted for 12 hours before autopsy.

Brown adipose tissue was taken from each test group and fixed in 10% neutral formalin. Following paraffin embedding, the paraffin-embedded tissue was sliced to 3-μm thickness using a microtome, stained with hematoxylin (10029273, DAKO, USA) and eosin (075K4346, Sigma-Aldrich, USA) (H&M), and observed under an optical microscope. The result is shown in FIG. 12.

Figure 12:
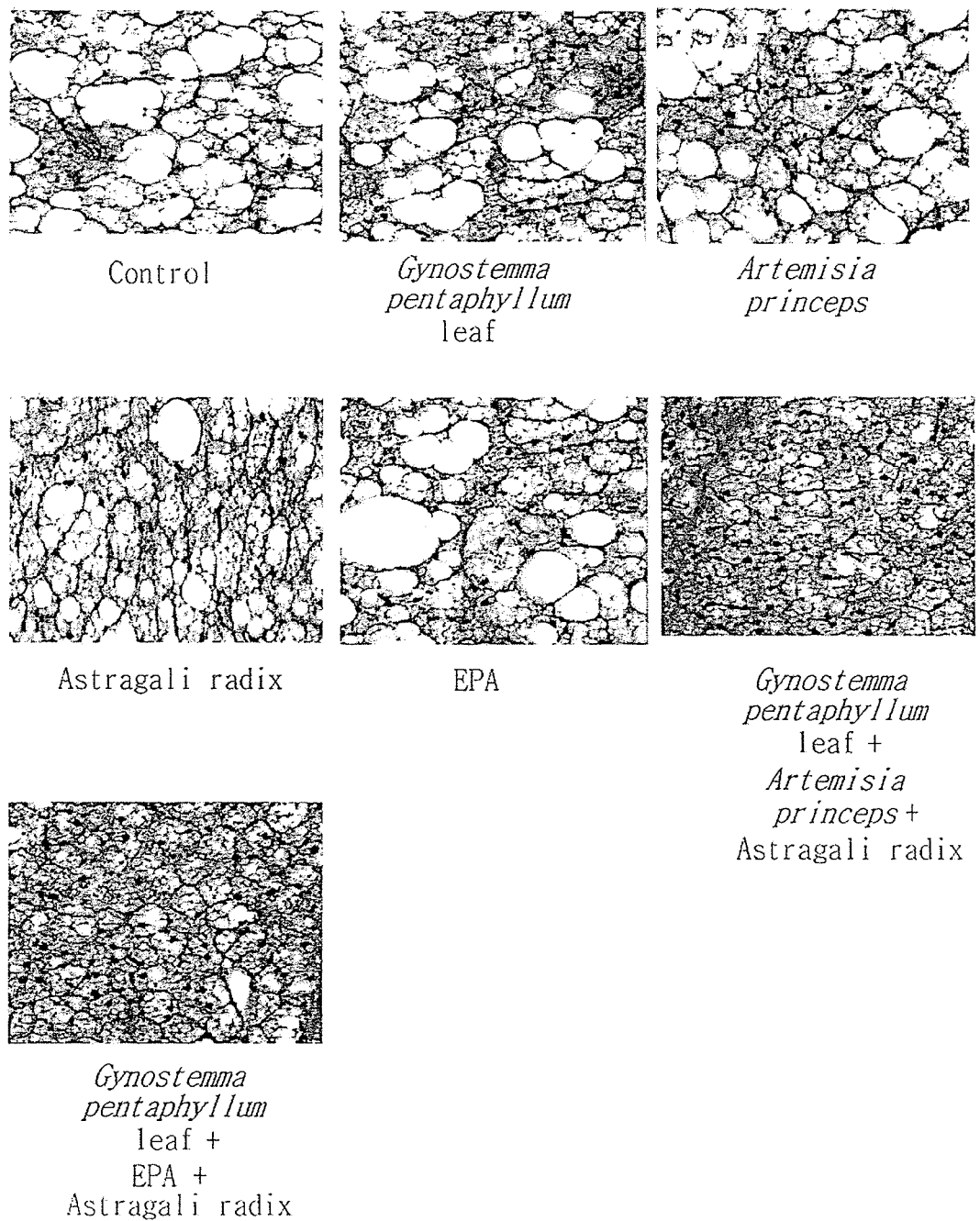
FIG. 12 shows the size of lipid droplets in brown adipose tissue of groups to which *Artemisia princeps* extract, EPA, *Gynostemma pentaphyllum* leaf extract, astragali radix extract or mixtures thereof were administered.

As seen from FIG. 12, the group to which the mixture of *Gynostemma pentaphyllum* leaf extract, *Artemisia princeps* extract and astragali radix extract or the mixture of *Gynostemma pentaphyllum* leaf extract, EPA and astragali radix extract was administered showed lipid droplets of remarkably decreased size in the brown adipose tissue as compared to the untreated negative control group or the groups to which the test substances were administered alone.

Accordingly, it can be seen that administration of a mixture of the substances that activate PPAR-δ, AMPK and PGC1-α respectively may reduce the size of lipid droplets in brown adipose tissue.

Test Example 12

Evaluation of Gene Expression in Muscle Cells
(Individual Level)

5-week-old male C57BL/6 mice were grouped with 10 mice per group. The experimental mice were orally administered with *Gynostemma pentaphyllum* leaf extract, *Artemisia princeps* extract, astragali radix extract or EPA alone, a mixture of *Artemisia princeps* extract, *Gynostemma pentaphyllum* leaf extract and astragali radix extract or a mixture of EPA, *Gynostemma pentaphyllum* leaf extract and astragali radix extract (200 mg/kg) as test substances for 8 weeks, once a day, and then gene expression level in muscle cells was evaluated. The mice were fasted for 12 hours before autopsy.

Muscle taken from each test group was dissected and RNA was extracted using the TRIzol reagent (Invitrogen). cDNA was synthesized using the extracted and quantitated RNA (1 μg/μL) and a reverse transcription system (Promega). Expression profile of the CPT1β, PDK4, PGC1α and GAPDH genes was measured using the synthesized cDNA and primers and probes (Applied Biosystems; CPT1β, Mm00487200_m1; PDK4, Mm00447181_m1; PGC1-α Mm00447181_m1; GAPDH, Mm99999915_q1) designed for the genes. PCR and analysis were performed using the Rotor-Gene 3000 system (Corbett Research, Sydney, Australia). The result is shown in FIG. 13.

Figure 13:
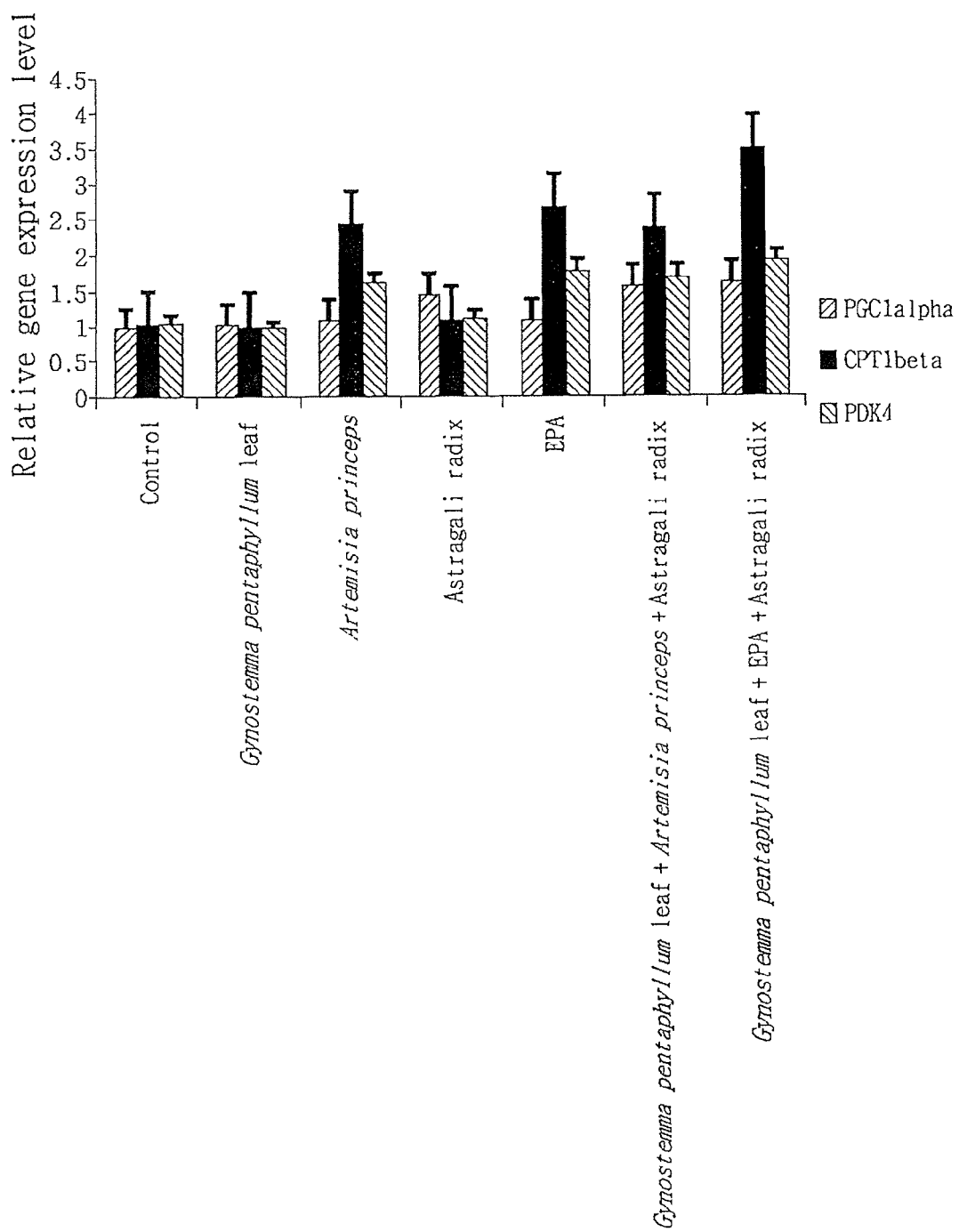
FIG. 13 compares the expression level of the CPT1β, PDK4 and PGC1-α genes in the muscle cells of groups to which *Artemisia princeps* extract, EPA, *Gynostemma pentaphyllum* leaf extract, astragali radix extract or mixtures thereof were administered relative to a negative control.

As seen from FIG. 13, the group to which the mixture of *Gynostemma pentaphyllum* leaf extract, *Artemisia princeps* extract and astragali radix extract or the mixture of *Gynostemma pentaphyllum* leaf extract, EPA and astragali radix extract was administered showed about 2 times increased expression of the genes as compared to the untreated negative control group or the groups to which the test substances were administered alone. Accordingly, it can be seen that administration of a mixture of the substances that activate PPAR-δ, AMPK and PGC1-α respectively may promote fat and sugar metabolism in muscle.

Formulation examples of the pharmaceutical composition, food composition and beauty care composition according to the present disclosure comprising the PPAR-δ activating substance, the AMPK activating substance and the PGC1-α activating substance as an active ingredient are described hereinafter. However, the scope of the present disclosure is not limited to the following examples.

Formulation Example 1

Preparation of Tablet

| | |
|---|---|
| Example 1 or Example 2 | 50 mg |
| Corn starch | 100 mg |
| Lactose | 100 mg |
| Magnesium stearate | 2 mg |
| Vitamin C | 50 mg |

The above ingredients are mixed and prepared into a tablet according to a commonly employed method.

Formulation Example 2

Preparation of Capsule

| | |
|---|---|
| Example 1 or Example 2 | 50 mg |
| Corn starch | 100 mg |
| Lactose | 100 mg |
| Magnesium stearate | 2 mg |
| Vitamin C | 50 mg |
| Serine | 50 mg |

The above ingredients are mixed and filled in a gelatin capsule to prepare a capsule according to a commonly employed method.

Formulation Example 3

Preparation of Liquid

| | |
|---|---|
| Example 1 or Example 2 | 100 mg |
| High-fructose corn syrup | 10 g |
| Mannitol | 5 g |
| Vitamin C | 50 mg |
| Serine | 50 mg |
| Fat | adequate |
| Purified water | balance |

According to a commonly employed method, the above ingredients are dissolved by adding to purified water. After adding an adequate amount of lemon flavor, the ingredients are mixed and purified water is added to make a total volume 100 mL. The mixture is filled in a brown bottle and sterilized to prepare a liquid.

Formulation Example 4

Preparation of Health Food

| Example 1 or Example 2 | 1000 mg |
|---|---|
| Vitamin mixture | |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Mineral mixture | |
| Ferrous sulfate | 1.75 mg |
| Zinc oxide | 0.82 mg |
| Magnesium carbonate | 25.3 mg |
| Potassium phosphate monobasic | 15 mg |
| Calcium phosphate dibasic | 55 mg |
| Potassium citrate | 90 mg |
| Calcium carbonate | 100 mg |
| Magnesium chloride | 24.8 mg |

The compositions of the vitamin and mineral mixtures are presented as an example appropriate for health food. However, the compositions can be varied differently. According to a commonly employed method, the above ingredients are mixed, prepared into granule and then used for preparation of a health food composition.

Formulation Example 5

Preparation of Drink

| Example 1 or Example 2 | 1000 mg |
|---|---|
| Citric acid | 1000 mg |
| Oligosaccharide | 100 g |
| Plum concentrate | 2 g |
| Taurine | 1 g |
| Purified water | to make 1000 mL |

According to a commonly employed method, the above ingredients are mixed and heated at 85° C. for about 1 hour while stirring. Thus prepared solution is filtered, collected in a sterilized 2-L container, sealed, and then stored in a refrigerator, for use in preparation of a drink composition.

Formulation Example 6

Preparation of Cream

A cream is prepared using the ingredients described in Table 3 according to a commonly employed method.

TABLE 3

| Ingredients | wt % |
|---|---|
| Example 1 or Example 2 | 2.0 |
| Polysorbate 60 | 1.5 |
| Sorbitan sesquiolate | 0.5 |
| PEG60 hydrogenated castor oil | 2.0 |
| Liquid paraffin | 10 |
| Squalane | 5.0 |
| Caprylic/capric triglyceride | 5.0 |
| Glycerin | 5.0 |
| Butylene glycol | 3.0 |
| Propylene glycol | 3.0 |
| Triethanolamine | 0.2 |
| Antiseptic | adequate |
| Pigment | adequate |
| Flavor | adequate |
| Purified water | to 100 |

The invention claimed is:

1. A method for strengthening a weakened muscle in a human in need thereof consisting essentially of administering therapeutically effective amounts of a component selected from the group consisting of *Artemisia princeps* extract, black pepper extract, and green mate extract, a component selected from the group consisting of *Gynostemma pentaphyllum* leaf extract, *Citrus unshiu* extract and *Houttuynia cordata* extract, and a component selected from the group consisting of astragali radix extract, puerariae flos extract and *Citrus leiocarpa* extract to said human to strengthen the weakened muscle in the human in need thereof.

2. The method of claim 1, wherein the component selected from the group consisting of *Artemisia princeps* extract, black pepper extract, and green mate extract, the component selected from the group consisting of *Gynostemma pentaphyllum* leaf extract, *Citrus unshiu* extract and *Houttuynia cordata* extract, and the component selected from the group consisting of astragali radix extract, puerariae flos extract and *Citrus leiocarpa* extract are mixed at a ratio of 1-10: 1-10 : 1-10.

* * * * *